Nov. 18, 1952 W. T. KIRKMAN Plant Pat. 1,147
PEACH TREE
Filed Oct. 20, 1951
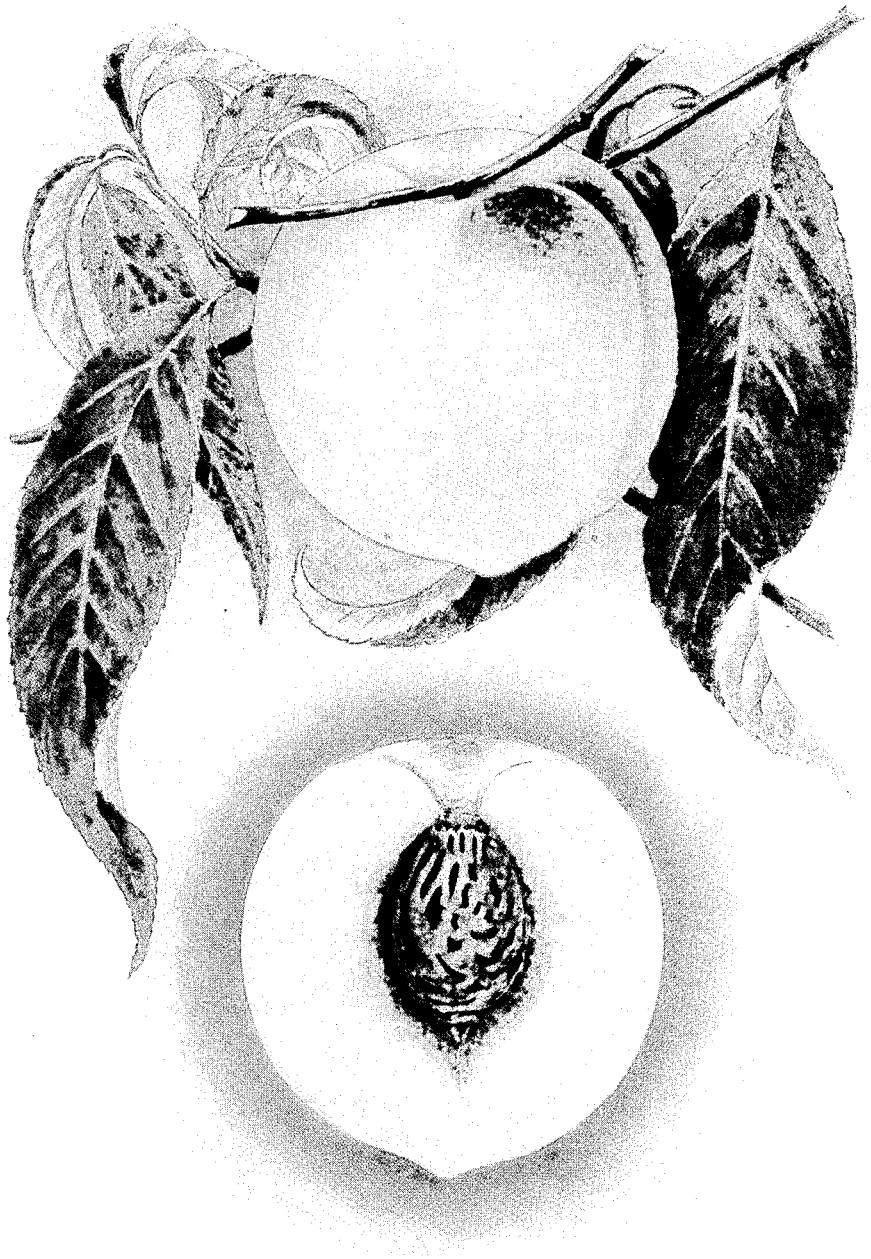
WITNESS
Addison E. Avery
INVENTOR
William T. Kirkman
BY Webster & Webster
ATTYS.

Patented Nov. 18, 1952

Plant Pat. 1,147

UNITED STATES PATENT OFFICE 1,147

PEACH TREE

William T. Kirkman, Madera, Calif.

Application October 20, 1951, Serial No. 252,337

1 Claim. (Cl. 47—62)

This discovery relates to a new and distinct variety of peach tree which bears large freestone fruit which is yellow skinned, washed and dotted medium red over a major portion, and having apricot yellow flesh streaked with red adjacent the stone cavity, the fruit—in quality and general coloring—resembling that of the parent variety, Kirkman Gem peach (United States Plant Patent No. 506).

As distinguished from the Kirkman Gem peach the present variety ripens approximately two to three weeks earlier; i. e. about the 20th of August in a normal year, thus making the fruit available on the market in a period between the Rio Oso Gem peach (United States Plant Patent No. 84) and the Kirkman Gem peach aforesaid. This is a distinct and important commercial advantage.

Another novel feature of the present variety of peach tree is that the fruit is more fully red over-colored at maturity than the fruit of the Kirkman Gem peach.

The Kirkman Gem peach and the present variety can be further distinguished by reason of the absence here of the dark reddish or brownish suture and the tendency to be flat or truncate at the stem end, both of which characterize the former.

The instant variety originated as a mutation (bud sport) on a Kirkman Gem peach tree in my experimental orchard near Madera, California. Such orchard is under continuing and careful inspection, and in the course of such activities the present mutation was recognized as having new and distinct features, particularly with respect to its ripening period.

Subsequent to discovery of the instant variety it has been successfully asexually reproduced by budding onto root stock trees in my orchard aforesaid.

In the drawings:

Fig. 1 is a perspective view of one of the fruit in association with twigs and leaves.

Fig. 2 is a transverse sectional elevation of the fruit.

Referring now more specifically to the pomological details of this new and distinct variety of peach tree, the following is an outline description thereof; all major color plate identifications being by reference to Maerz and Paul Dictionary of Color.

Tree: Closely similar in shape and growing characteristics to the Kirkman Gem variety.

*Current growth.*—Medium stoutness, green or reddish where exposed; buds plump, ovate, appressed; scales dark brown with heavy greyish pubescence.

*Two-year wood.*—Greenish-brown, with numerous light brown, corky, raised lenticels.

Flowers: Large; pink; bloom with Kirkman Gem.

Leaves: Color—medium green (22–L–7 to 22–L–8).

Shape and size—lanceolate; length 4½ to 5 inches, width 1¼ to 1⅜ inches.

*Base.*—Acute to nearly rounded.

*Apex.*—Long—acuminate.

*Blade.*—Flat to slightly wavy; medium thickness; color green both surfaces; straight to recurved; midrib shallowly channeled on the upper surface, raised below; lateral reins slightly raised below. Margin finely serrate to crenate—minutely gland tipped.

*Glands.*—Reniform; 1 to 3 in number, alternate or opposite; usually borne on the base of the blade.

*Petiole.*—Short, stout; approximately ⅜ inches; strongly U-channeled on the upper side.

Fruit:

*Shape.*—Oval, slightly pointed (in suture aspect shape is ovate); one half usually slightly larger; length approximately 2½ inches, cheek diameter approximately 3⅜ to 3½ inches, suture diameter approximately 3⅜ inches. Shape smooth and nearly regular.

*Base.*—Round in outline; approximately 1⅛ inches across and (cavity) 8/8 inch deep.

*Cavity.*—Deep, conic to acuminate-conic.

*Shoulders.*—Rounded, cleft at the suture.

*Apex.*—Blunt—pointed.

*Suture.*—A shallow but well-marked groove from base to apex, but not running past the apex; slightly roughened; cleft at the base through the cavity shoulder; one suture lip usually larger medianly.

*Ground-color.*—Yellow (10–K–3 to 9–L–8).

*Pubescence.*—Thick, short, fine.

Flesh:

*Color.* — Light apricot-yellow (G–K–4 to 9–L–7, with red streaking into the flesh from the stone cavity for a short distance only (53–L–8).

*Stone cavity.*—Aspect bright red; moderately sculptured, fibers bright red.

*Flavor.*—Very good; subacid, sprightly, moderately sweet.

*Texture.*—Firm-melting type, but quite firm, fine-grained, excellent.

Stone:

*Shape.*—Long-oval; length approximately 1⅜ inches, cheek diameter approximately ¾ inch, suture diameter approximately 1 inch.

*Base.*—Grossly short-necked; stem scar medium size or smaller, ovalish-round in outline, slightly oblique to the ventral suture (edge).

*Apex.*—Round-pointed, with a medium thick, acuminate, sharp tip.

*Sutures.*—Dorsal—somewhat raised, especially medianly, evenly curved medianly, but straight to slightly recurved to the tip apically; narrowly V-grooved from the base to the middle, closed or very narrowly slit-grooved from the middle to the apex; the groove sides interrupted by the surface markings. Ventral—low, narrow to medium width, an irregularly multiple-grooved flange, becoming narrower toward the apex—the grooved shallow to medium depth; the flange blunt, usually slightly higher basally and apically, curved from the base to apex, tending to be flattened in the mid-portion. The lateral grooves close to wide, of medium depth, continuous from the base to apex, with the outer side interrupted by the surface markings.

*Surface markings.* — Grossly and deeply grooved on the cheeks and apically, with the ridges rounded and blunt; pitted on the basal portion or neck only.

*Color.*—Dark brown (7–A–12 to 7–H–12), tinged with red at the base and along the suture edges from the base.

*Kernel.*—Brown, plump, oval to slightly ovate, bitter.

Eating quality: Good.

Shipping quality: Good.

Use: Local market; dessert; canning; freezing; and long-distance shipping.

The tree and its fruit herein described may vary in slight detail due to climatic and soil conditions under which the variety may be grown.

Having thus described my discovery, I claim:

A new and distinct variety of peach tree as described and illustrated, characterized by large freestone fruit having a ripening period intermediate the Rio Oso Gem peach and the Kirkman Gem peach, being approximately two to three weeks earlier than the latter; such fruit being yellow in ground color, washed and dotted medium red over a major portion of the surface and to a much greater extent than said Kirkman Gem peach; having apricot-yellow flesh, with the stone cavity red streaking a distance into the flesh; and being oval as compared to the round-truncate fruit of the Kirkman Gem peach.

WILLIAM T. KIRKMAN.

No references cited.